(12) United States Patent
Criscione et al.

(10) Patent No.: US 8,187,160 B2
(45) Date of Patent: **\*May 29, 2012**

(54) DEVICE FOR PROACTIVE MODULATION OF CARDIAC STRAIN PATTERNS

(75) Inventors: John C. Criscione, College Station, TX (US); Saurabh Biswas, College Station, TX (US)

(73) Assignee: The Texas A&M University System, College Station, TX (US)

( \* ) Notice: Subject to any disclaimer, the term of this patent is extended or adjusted under 35 U.S.C. 154(b) by 715 days.

This patent is subject to a terminal disclaimer.

(21) Appl. No.: 12/242,197

(22) Filed: Sep. 30, 2008

(65) Prior Publication Data

US 2009/0036730 A1 Feb. 5, 2009

Related U.S. Application Data

(63) Continuation of application No. 10/870,619, filed on Jun. 17, 2004, now Pat. No. 7,445,593.

(60) Provisional application No. 60/479,625, filed on Jun. 18, 2003.

(51) Int. Cl.
*A61N 1/362* (2006.01)

(52) U.S. Cl. ........................................... 600/16

(58) Field of Classification Search ............... 600/16–18, 600/37
See application file for complete search history.

(56) References Cited

U.S. PATENT DOCUMENTS

| | | | |
|---|---|---|---|
| 2,826,193 A | 3/1958 | Vineberg |
| 3,034,501 A | 5/1962 | Hewson |
| 3,233,607 A | 2/1966 | Bolie |
| 3,513,836 A | 5/1970 | Sausse |
| 4,048,990 A | 9/1977 | Goetz |
| 4,536,893 A | 8/1985 | Parravicini |
| 5,119,804 A | 6/1992 | Anstadt |
| 5,256,132 A | 10/1993 | Snyders |
| 5,749,839 A | 5/1998 | Kovacs |
| 5,863,574 A | 1/1999 | Julien |
| 6,224,540 B1 | 5/2001 | Lederman et al. |
| 6,387,042 B1 | 5/2002 | Herrero |

(Continued)

FOREIGN PATENT DOCUMENTS

WO 9922784 A1 5/1999

OTHER PUBLICATIONS

Anstadt, M.P., et al., "Non-blood contacting biventricular support for severe heart failure." Ann Thorac Surg (2002), 73:556-62.

(Continued)

*Primary Examiner* — John Lacyk
(74) *Attorney, Agent, or Firm* — Chainey P. Singleton; Edwin S. Flores; Chalker Flores, LLP

(57) ABSTRACT

A direct cardiac assist device which may aid in ventricular recovery. The device proactively modulates cardiac strain pattern to produce a contraction strain pattern that induces beneficial growth and remodeling of the myocardium or prevents or reduces apoptosis of the myocytes. The device may include an outer shell, membrane, or mesh and an inner membrane. The space between the outer member and the membrane may be filled with fluid that is pressurized during contraction. The device prescribes a beneficial strain pattern during heart contraction. This strain pattern does not invert the curvatures or grossly alter the curvatures of the heart and may assist in myocyte regrowth and healing of the failing heart.

17 Claims, 6 Drawing Sheets

U.S. PATENT DOCUMENTS

| | | | |
|---|---|---|---|
| 6,540,666 | B1 | 4/2003 | Chekanov |
| 6,592,619 | B2 | 7/2003 | Melvin |
| 6,595,912 | B2 | 7/2003 | Lau et al. |
| 6,602,182 | B1 | 8/2003 | Milbocker |
| 6,602,184 | B2 | 8/2003 | Lau et al. |
| 6,612,978 | B2 | 9/2003 | Lau et al. |
| 6,612,979 | B2 | 9/2003 | Lau et al. |
| 6,663,558 | B2 | 12/2003 | Lau et al. |
| 6,784,283 | B2 | 8/2004 | Anderson et al. |
| 7,445,593 | B2 * | 11/2008 | Criscione .................. 600/16 |
| 7,494,459 | B2 | 2/2009 | Anstadt et al. |
| 7,935,045 | B2 | 5/2011 | Criscione |
| 2002/0665449 | | 5/2002 | Wardle |

OTHER PUBLICATIONS

Artrip, J.H., et al., "Physiological and hemodynamic evaluation of nonuniform direct cardiac compression." Circulation (1999), 100(suppl II):236-43.

Dipla, K., et al., "Myocyte recovery after mechanical circulatory support in humans with end-stage heart failure." Circulation (1998), 97:2316-2322.

Goldstein, D.J., et al., "Medical progress: implantable left ventricular assist devices." N Engl J Med (1998), 339 (21):1522-1533.

Heerdt, P.M., et al., "Chronic unloading by left ventricular assist device reverses contractile dysfunction and alters gene expression in end-stage heart failure." Circulation (2000), 102:2713-2719.

Karvarana, M.N., et al., "Circulatory support with a direct cardiac compression device: a less invasive approach with the AbioBooster device." J Thorac Cardiovasc Surg (2001), 122:786-787.

Kawaguchi, O., et al., "Mechanical enhancement of myocardial oxygen saving by synchronized dynamic left ventricular compression." J Thorac Cardiovasc Surg (1992), 103:573-81 (Abstract).

Kherani, A.R., et al., "Ventricular assist devices as a bridge to transplant or recovery." Cardiol (2004), 101:93-103.

Omens, J.H. "Stress and strain as regulators of myocardial growth." Prog. Biophys. Molec. Biol. (1998), 69:559-572.

Oz, M.C., et al., "Direct cardiac compression devices." J Heart Lung Transplant (2002), 21:1049-1055.

Rose, E.A., et al., "Long-term use of left ventricular assist device for end-stage heart failure." N Engl J Med (2001), 345(20):1435-1443.

Williams, M.R., and Artrip, J.H. "Direct cardiac compression for cardiogenic shock with the CardioSupport System." Ann Thorac Surg (2001), 71:S188-9.

Cohn, Jay N., "Cardiac Remodeling Concepts and Clinical Implications: A Consensus Paper from an International Forum on Cardiac Remodeling,"Journal of American College of Cardiology, vol. 35, No. 3, XP-002302310, pp. 569-582, Mar. 2000.

International Search Report for PCT/US2004/019809, dated Oct. 25, 2004.

International Search Report for PCT/US2005/03343, dated Jul. 16, 2007.

International Search Report for PCT/US2008/071618, dated Feb. 12, 2009.

* cited by examiner

DEVICE FOR PROACTIVE MODULATION OF CARDIAC STRAIN PATTERNS

PRIORITY CLAIM

The present application is a continuation of U.S. patent application Ser. No. 10/870,619, filed Jun. 17, 2004. The contents of each of which are incorporated by reference herein in their entireties. The present application claims priority under 35 U.S.C. §119(e) to U.S. Provisional Patent Application Ser. No. 60/479,625 filed Jun. 18, 2003.

TECHNICAL FIELD

The present invention is related in general to a direct cardiac compression device. In particular is a direct cardiac compression device that proactively modulates the strain pattern in the heart during contraction so as to reduce apoptosis in the myocardium and/or induce beneficial growth and remodeling of the myocardium and/or scarred regions. In particular, the device of the present invention does not invert or grossly perturb the curvature of the heart during contraction. In so doing this invention may promote recovery of the heart from injury, ischemia, infarction, infection, and/or congestive heart failure; and when combined with pharmacotherapy, pacing, electrical resynchronization, surgical reconstruction, stem cell therapy, gene therapy, and/or other therapies, it may further enhance recovery of the heart.

BACKGROUND OF THE INVENTION

Congestive heart failure (CHF) is a debilitating condition that afflicts 4.8 million Americans with an increasing incidence. Despite efforts at preventative cardiac care, the incidence of CHF is increasing because the average age of survival in the population is increasing and because more people are surviving their first heart attack. Pharmacological therapy and electrical stimulation therapies are improving, yet many patients still reach end-stage heart failure. Heart transplant is available for some patients with the most severe heart failure, however the supply of donor hearts is not adequate to meet demand and there are many complications associated with immunosuppression. Aberrant growth and remodeling are evident in CHF, and it is likely that growth and remolding are primary contributors to infarct expansion, myocardial scarring, and ventricular rupture.

Recent studies show that effective (i.e., physiological) growth and remodeling of the heart's muscular tissue can reverse and cure CHF in some patients. Such a cure of CHF is called "ventricular recovery" herein, yet in some literature it is called reverse remodeling. The mechanism of ventricular recovery is a current and active area of research for the treatment of CHF. Hormonal and electro-physiological factors may play an important role. In addition, the influence of ventricular loading conditions on CHF is a significant factor. Unloading the diseased heart may decrease end-systolic volume and may create a more physiological strain pattern of the heart. A physiological strain pattern during contraction (also called "systole") may lead to ventricular recovery, and it may prevent infarct expansion, myocardial scarring, and/or ventricular rupture.

Further evidence for a potential, fundamental role of strain in cardiac physiology and pathophysiology is that myocytes are highly sensitive to strain and respond with altered gene expression. (See Komuro and Yazaki, Ann. Rev. Physiol. 55:55-75 (1993) and Sadoshima and Izumo, Ann. Rev. Physiol. 59:551-571 (1997).) Numerous investigations have shown that altered hemodynamic loading and/or heart disease lead to growth and remodeling of myocytes and their extracellular matrix. It is also known that failing hearts exhibit a patho-physiological strain pattern where hoop strain and apex-base stain are more equal than normal and heart wall thickening during contraction is globally less than normal and more uniform across the wall. Although there is still debate on what is the normal motion or strain pattern during contraction, current results show a strain pattern wherein hoop strain is greater than apex-base strain and greater wall thickening is seen on the inner wall of the heart as compared to the outer wall.

Thus the present invention includes a method of restoring a more normal physiological strain pattern to a dyskinetic or failing heart, i.e. a heart with a patho-physiological strain pattern. By doing so, myocytes may be induced to grow in a normal manner. The effects on stress and strain on myocyte growth is described in greater detail in J. H. Omens, "Stress and strain as regulators of myocardial growth", Prog. Biophys. Mol. Biol., 69 (2-3:559-72 (1998).

Despite the promise shown by growth and remodeling of damaged or diseased heart tissue, there have been no known attempts to proactively modulate the strain pattern during contraction. Instead, treatments have been focused on ways to increase blood flow, off-load the heart, and/or reduce wall stress. These methods include some blood contacting assist devices, surgical reconstruction of the ventricle(s), cardiomyoplasty, and surgical insertion of passive devices. These treatments may promote a more healthy type of strain pattern during contraction, yet they do so indirectly if at all.

Current devices that provide direct mechanical assistance to the heart itself are often called direct cardiac compression devices (DCCDs), and they do modulate directly the kinematics during contraction. Yet current DCCDs do not proactively modulate the strain pattern so as to guide heart recovery and/or myocardial recovery. In contrast, many devices may cause detrimental remodeling and/or apoptosis because the induced strain pattern is so grossly abnormal. As is clear from the various patents and papers on these devices, current DCCDs have been optimized to promote systolic ejection, to be implanted easily, to reduce thrombo-embolic complication, to closely fit the heart contours during diastole, and criteria other than systolic strain pattern modulation.

An extremely important aspect of contraction strain pattern is the fact that it depends on both the end-diastolic configuration (reference configuration) AND the end-systolic configuration (current configuration). The strain field is a function of the gradient (with respect to reference position) of the mapping of material points from the reference configuration to the current configuration. Thus, the fact that prior DCCDs have tried to fit well the diastolic configuration is inconsequential to achieving an appropriate contraction strain pattern because their end-systolic configurations are either grossly aberrant or unknown.

First, an early DCCD (called a cardiac massager because it was designed for use in open chest surgery and not for implantation) developed by Vineberg is described in U.S. Pat. No. 2,826,193 (the Vineberg patent). This device, when inflated, produces a systolic state with low (or even inverted) curvature in the circumferential-radial plane of the heart (FIG. 2, Vineberg patent) and in the longitudinal-radial plane (FIG. 3, Vineberg patent). This is caused by the two opposite chambers which, when inflated, induce hourglass-like systolic geometries (FIG. 5, Vineberg patent). Thus the Vineberg device induces an aberrant strain pattern during contraction.

A later device, the Anstadt cup, is described in U.S. Pat. No. 5,119,804 (the Anstadt patent). This device induces an inverted curvature of the longitudinal-radial plane during systole, but does retain a normal circumferential-radial plane curvature during systole (FIGS. 8, 9, and 10 Anstadt patent). The CardioSupport System made by Cardio Technologies, Inc. is similar to the Anstadt cup and also induces curvature inversion in the longitudinal-radial plane.

Whereas the Anstadt cup inverts curvature in the longitudinal-radial plane, the heart booster (U.S. Pat. No. 5,713,954 and Ann. Thorac. Surg. 68:764-7) inverts curvature in the circumferential-radial plane, but not in the longitudinal-radial plane (FIGS. 1 and 2, Ann. Thorac. Surg. 68:764-7). This device prescribes a gear-like geometry with numerous spurs. Each spur in this end-systolic geometry induces curvature inversion during systole.

The Anstadt cup and heart booster attach to the apex of the heart, while the Vineberg device attaches to the base through a draw string constrictor at the valve plane. However, many other DCCDs attach to the interventricular grooves and either pull on the grooves (for example, the AbioBooster by Abiomed, Inc., Danvers, Mass. as described by Karvana et al., 2001, and the DCC Patch by Heart Assist Technologies, New South Wales, Australia) or hold them static (for example the device in U.S. Pat. No. 4,536,893 of Parravicini, the "Parravicini patent"). In either case, pulling or holding the grooves static likely decreases the curvature in the circumferential-radial plane during systole whereas for normal hearts curvature increases as the diameter decreases during systole. (Note that the radius-of-curvature R is the inverse of curvature C, i.e. $C=1/R$). Nevertheless, it is uncertain what the systolic configuration is for these devices because it is not disclosed.

The Abiobooster and DCC Patch cover one ventricle of the heart, and it is likely that when pressurized they decrease the curvature of the free wall and septum. The Parravicini device is sutured to the interventricular groove (or sulcus) and either pulls on the grooves using the two opposing membranes or is held static by the outer rigid shell. Again, the exact mode of operation is not clear from the Parravicini patent because a systolic configuration is not shown. In either case, the resulting strain pattern is not proactively modulated and a decrease in curvature likely occurs during contraction.

One embodiment (shown in FIG. 3, but not FIGS. 1 and 2) of the Hewson device shown in U.S. Pat. No. 3,034,501 (the Hewson patent) is similar to the Vineberg and Parravicini devices in that two opposing membranes squash the heart and tend to flatten it between the opposing membranes (i.e. induce a systolic configuration with decreased curvature in much of the circumferential-radial plane yet with dramatically increased curvature on the edges where the two membranes attach to the device). However, a systolic configuration is not shown.

Similarly, a systolic configuration is not shown for the embodiment of the Hewson device in FIGS. 1 and 2 of the Hewson patent. To derive a systolic configuration, one must consider a force balance with the pneumatic chamber pressurized. Upon doing a force balance, however, one realizes that the Hewson embodiment 1 is unrealistic and not implantable. A pressure P in the pneumatic chamber will induce at least an upward force of PA where A is the cross-sectional area of the opening rim. If there are tensile membrane stresses the upward force will be higher. Hewson suggests that contact forces between the rim and the heart are supposed to hold the heart in place, yet even active hearts are soft tissues that can undergo high shear and slip out of the Hewson device. Moreover, it is now known that myocardium is organized into sheets that allow contracting myocytes to rearrange and shear to attain high radial strains—i.e., motions that would allow the heart to slip out of the Hewson device. A hypocontractile or failed heart would be even more likely to slip out because it would more easily permit radial stain.

To evaluate this problem, a device similar to that of Hewson was constructed and implanted in a young bovine. Ultrasound measurements of the actual animal were used to precisely size the device. Even with normal contractility (i.e. high stiffness), the heart readily escaped from the/device. The valve plane had to be sewn to the device and held in place with a stent that went from the device through the transverse pericardial sinus and pushed down on the commisure of the aortic and bicuspid valves.

Although a number of DCCDs are described above, other examples may be known to one skilled in the art. However, all current operable DCCDs suffer from a tendency to increase or even invert the curvature of the heart and thus produce an aberrant strain pattern during contraction.

SUMMARY OF THE INVENTION

The present invention includes a DCCD that proactively modulates the cardiac strain pattern during contraction or systole. Proactive modulation of cardiac strain pattern 5 includes active promotion of a strain pattern that induces growth and remodeling of the myocardium, diseased myocardium and/or scarred myocardium to more closely resemble a healthy myocardium and/or that reduces apoptosis in the myocardium. In all embodiments of the invention, the strain pattern during systole is proactively modulated. Although clinical trials and animal experiments with this invention will determine what strain pattern is more beneficial, current results suggest that the native strain pattern should be restored which is one with circumferential strain more negative than apex-base strain and with radial strain highest on the inner wall. In general, devices of the present invention do not invert the curvature or greatly perturb the curvature of the heart during contraction. The invention also may maintain the normal curvatures or strain pattern during diastole, or relaxation of the heart.

In one embodiment, the DCCD includes a membrane or mesh that encompasses the heart and that undergoes a shape change from an end-diastolic configuration to an end-systolic configuration and back again. These configurations and the way in which the shape change occurs are designed to promote a beneficial strain pattern in the heart during contraction.

In a further embodiment, the DCCD may include an outer shell, membrane, or mesh and an inner membrane attached to the outer shell. A fluid, which may be pressurized, may be provided between the outer shell and inner membrane.

In still further embodiments, the DCCD may be installed around the ventricular portion of a heart. It may be anchored to the valve plane of the heart. The device may include a pneumatic drive operable to pressurize the fluid.

In certain embodiments of the device, the outer shell, membrane, or mesh may be rigid, or it may include an adjustable outer shell, membrane, or mesh and/or inner shell, membrane or mesh.

A DCCD of the present invention may be used to assist a heart by attaching the device to the heart. Attaching any DCCD as described above or otherwise within the scope of the present invention may also assist in: ventricular recovery, providing a normal physiological strain pattern to the heart, particularly during systole, promoting normal myocyte growth in the heart, preserving the myocardium in the border zone of acute infarcts, preventing ventricular rupture in the few days following a myocardial infarction, reducing scar formation and promoting growth of myocytes from native or injected myoblasts in infarcted heart tissue, restoring heart function after myocardial infarction, and generally promoting beneficial growth and remodeling of the cardiac tissue, particularly to attain ventricular recovery, in patients with heart insufficiency resulting from acute or chronic causes, inter alia.

DCCDs of the present invention may be employed for any of the uses described above, or for other uses in which a physiological strain pattern during systole is beneficial, by providing the device to a patient. This may be accomplished by opening the chest cavity of the patient to provide access to the heart and attaching the device to the heart. For devices that expand once inside the chest, they may be provided through a smaller incision or through a tube. In some embodiments, the device may be anchored to the valve plane of the heart.

BRIEF DESCRIPTION OF THE DRAWINGS

A more complete and thorough understanding of the present embodiments and advantages thereof may be acquired by referring to the following description taken in conjunction with the accompanying drawings.

FIG. 2 illustrates the construction of a prototype of an embodiment of the present invention. The prototype was built to fit the heart of a 110 kg young bovine into which the device was implanted for an acute period (2 hours) to test the valve plane attachment and the preservation of cardiac curvature during assist with varying degrees of heart failure (induced pharmacologically with high doses of a beta-blocker) Because the period of implantation was brief, biocompatible materials were not utilized; rather inexpensive and readily available materials were used.

DETAILED DESCRIPTION OF THE INVENTION

The present invention relates to a DCCD for proactive modulation of cardiac strain pattern. Proactive modulation of cardiac strain pattern according to the present invention 5 includes the active promotion by a DCCD of a strain pattern that induces growth and remodeling of the myocardium to more closely resemble a healthy myocardium or that reduces apoptosis in the myocardium.

In most embodiments of the invention, the strain pattern is a physiological strain pattern. A physiological strain pattern, for the purposes of the present invention, is one which does not invert the heart's curvature during systole. The invention may also maintain a normal curvature or strain pattern during diastole, or relaxation of the heart.

Such DCCDs may be formed in a variety of ways, but generally include a membrane or mesh that encompasses the heart and that undergoes a shape change from an end-diastolic configuration to an end-systolic one and back again. These configurations are such that they promote a desired strain pattern, such as one in which the epicardial contours or heart curvatures are optimized. Other aspects of strain such as cardiac twist mayor may not be modulated.

In one embodiment, there is an outer shell, membrane, or mesh, such as a rigid outer shell, attached to an inner membrane and filled with a fluid that may be pressurized during systole to assist the heart while preserving a beneficial strain pattern and not inverting the curvature of the heart.

Figure 1:
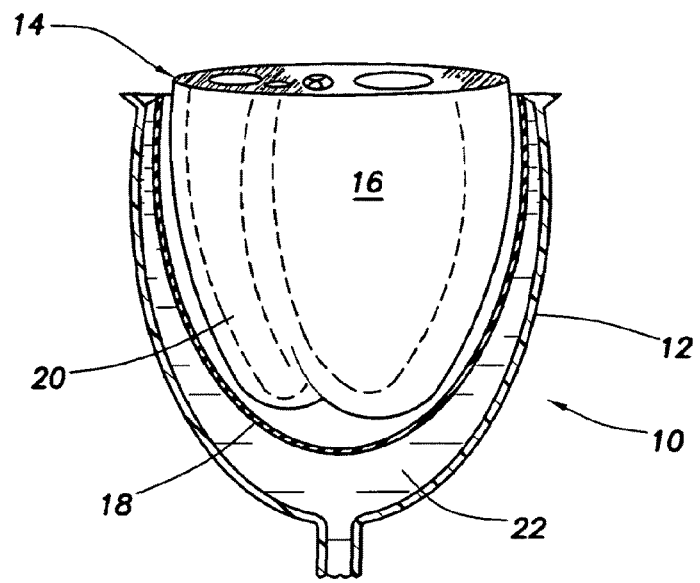
FIG. 1 illustrates an embodiment of the DCCD of the present invention applied to the ventricular surfaces of the heart.

In one embodiment of the present invention, the DCCD is designed to fit around the ventricular surface of the heart as shown in FIG. 1. Briefly, the DCCD 10 includes an outer rigid shell 12 attached to the valve plane 14 of the heart 16, a highly elastomeric membrane 18 which abuts the epicardial surface of the heart 20 and modulates extra-ventricular displacements, and fluid 22 between the shell 12 and membrane 18 which is pressurized during systole to assist the heart. The device may be run pneumatically, for example with a system similar to that used with the Anstadt cup. Methods of producing such a device are provided in Example 1.

Figure 5:
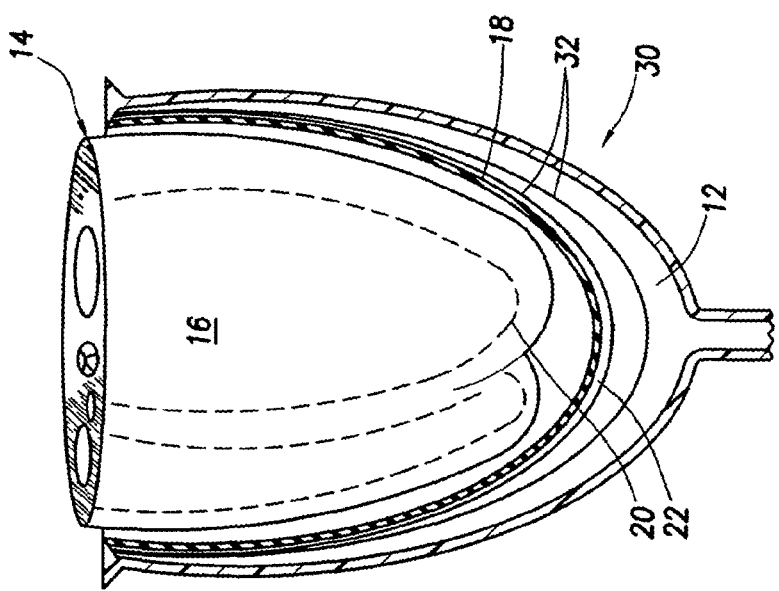
FIG. 5 illustrates an embodiment of the DCCD of the present invention applied to the ventricular surfaces of the heart.

In another embodiment of the present invention, a DCCD is designed to fit around the ventricular surface of the heart as shown in FIG. 5. The DCCD 30 is similar to that of FIG. 1, except that at least one additional woven component 32 is provided between the elastomeric membrane 18 and the shell 12. These woven components are referred to herein as "socks" 32 and preferably do not have a symmetrical weave. The socks 32 instead have a satin weave with a directional bias with more fibers in the apex-base direction to make the apex-base motion less than the circumferential motion. The weave may also have a helical component to give the heart a twist when it is in its dilated or diastole state. To increase the amount of anisotropy, longitudinal fibers in the socks may be thicker than circumferential ones. As the heart heals, at least partially as a result of the physiological strain patterns produced by the DCCD, and returns to normal size, the outer socks will collapse and not modulate the strain pattern. This gradually weans the healing heart from the DCCD.

In addition to the use of socks, the embodiment of the invention in FIG. 5 preferably uses a biocompatible inner membrane 34 abutting the epicardium 20. The membrane 34 may be isotropic and homogeneous. For example, a segmented polyurethane membrane as used in aortic balloons may be used. In order to produce a composite structure of membrane and socks that is anisotropic and heterogeneous and able to restore a physiological strain pattern to the heart, the socks 32 may be anisotropic and have a weave that may vary with circumferential and/or axial location.

Figure 6:
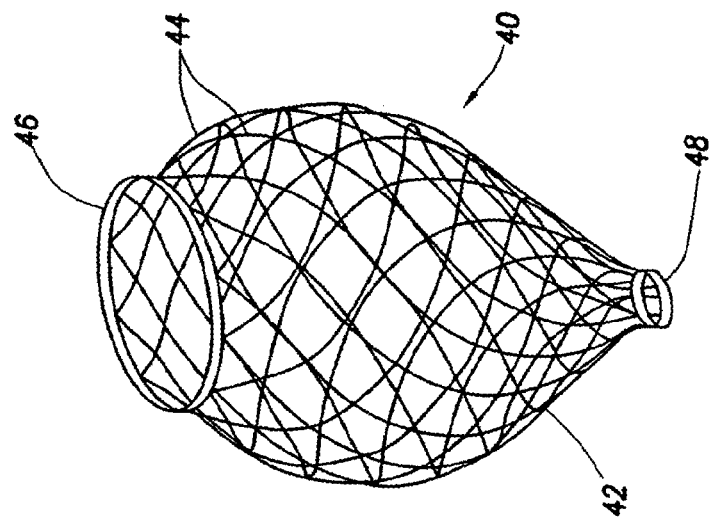
FIG. 6 illustrates an embodiment of the DCCD of the present invention with an adjustable outer shell.
Figure 7:
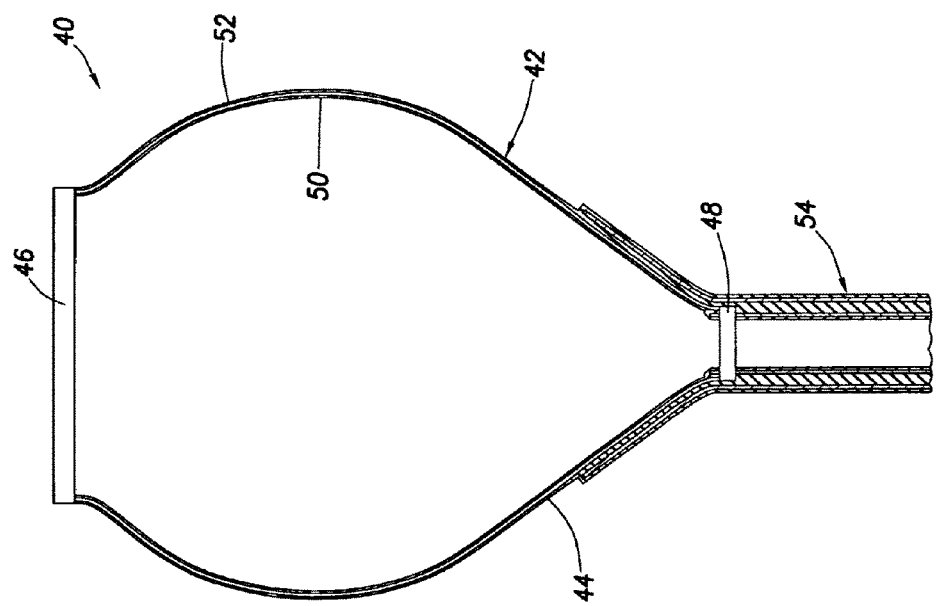
FIG. 7 illustrates a cut-away view of an embodiment of the DCCD of the present invention with an adjustable outer shell.

Yet another embodiment of the DCCD of present invention is shown in FIGS. 6 and 7. The embodiment 40 is adjustable as the diseased heart recovers. The embodiment lacks a rigid outer shell and instead includes an adjustable shell 42 formed from a series of rods 44 attached to a basal annulus 46 and attached to or passing through an apical annulus 48. The basal annulus 46 is designed to fit the valve plane of the heart, which does not vary significantly between diseased and non-diseased states. The rods 44 are bent to form a vase-shaped structure as shown in FIG. 6. Elastic membranes 50 and 52 may be used to seal the adjustable shell 42.

Specifically, one membrane 50 may be placed on the inside of the shell 42 and one on the outside 52, as shown in FIG. 7. These membranes 50 and 52 may be held in place by applying a negative pressure to the space in which the rods 44 lie. Use of larger numbers of rods minimizes puckering of the membranes 50 and 52 when pressure is applied between the shell and the inner membrane. The membranes 50 and 52 may be woven or non-woven.

To decrease the size of the shell 42 as the heart heals, the apical annulus 48 may be pulled into a flared tube-like structure 54 as shown in FIG. 7. Lead screws (not shown) may be used to pull on the apical annulus 48 and draw it into the tube 54. These screws may be turned using a custom designed catheter. When implanted in a human, the lower tube-like structure 54 may be placed along the inferior boundary of the left lung. A pneumatic driver (not shown) may be placed in the abdomen.

Figure 8:
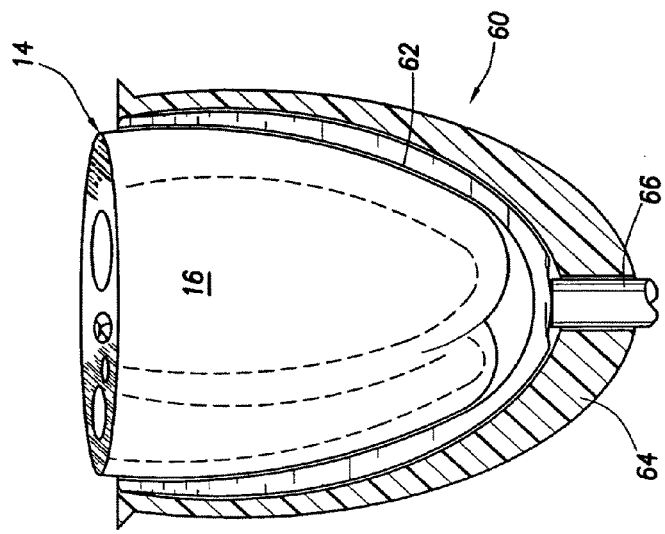
FIG. 8 illustrates an embodiment of the DCCD of the present invention applied to the ventricular surfaces of the heart.

Yet another embodiment of the DCCD of the present invention is shown in FIG. 8. In this embodiment the device 60 includes a functionally-graded membrane 62 surrounding the heart 16 with a hard shell 64 enclosing the membrane 62. The shell 64 may be attached to the valve plane 14. A magnetic piston 66 at the bottom of the shell 64 may be driven by a solenoid (not shown) to change the volume within the shell 64 and assist ejection and/or filling of the heart 16 with blood. There may be a permanent magnet (not shown) in the shell 64 so that the piston 66 is drawn outward to counteract the resting tension in the membrane 62 that surrounds the heart 16. An outer membrane filled with nitrogen or an inert fluid may be included to prevent body fluids from entering the solenoid-piston interface and to prevent the piston 66 from impacting or drawing in other organs (i.e. lung or diaphragm). The device 60 may also include wires and electrical components (not shown) that sense the electrocardiogram or pace the heart and simultaneously drive the piston 66 such that piston action and the heartbeat are synchronized.

In another embodiment of the present invention, not explicitly shown, the DCCD includes biocompatible chamber(s) that attach together and that slip over the apex of the heart and contain the ventricles. The chambers may be structured so as to take on shapes that proactively modulate systole strain patterns in a beneficial manner. They may also beneficially modulate diastolic strain patterns.

In other embodiments of the present invention, not explicitly shown, current devices may be modified to resemble the devices described above or to otherwise render them able to proactively modulate cardiac strain patterns during systole. For example, in all devices that pull on the interventricular grooves and in the Hewson device, the balance of forces may be examined to determine a systolic configuration geometry that will proactively modulation the strain pattern in accordance with the present invention.

For DCCDs that attach to the apex of the heart, such as the Anstadt and CardioSupport System, it is possible to make them proactive modulators of strain patterns according to the present invention by making the suction cup deformable and such that it preserves cardiac curvature when the air chambers are pressurized. For the heart booster, it is possible to make it a proactive modulator of contraction strain pattern by increasing the number of tubes so that the curvature inversion is insignificant or introduce a membrane that surrounds the heart and has a liquid between it and the tubes. The fluid will fill then flow into the spur regions rather than pull in the myocardium. Other ramifications are possible so long as the systolic configuration is optimized for strain pattern.

Other ramifications of existing devices are possible that optimize the systolic configuration to obtain a strain pattern in accordance with the present invention. In some embodiments, this may limit optimization for ejection of blood, a primary design goal in such devices. However, so long as a suitable amount of blood is ejected initially, thereby preventing serious harm to the patient, blood ejection will often improve as the myocardium heals in response to the physiological systolic strain patterns.

Various metals or other hard materials may be used to form components of selected embodiments of the present invention. In certain embodiments, titanium, Nitinol (a shape memory titanium/nickel alloy) and/or or hard biocompatible plastic may be used to from any rigid components. For example, titanium may be used to form stents because it is strong, light, and biocompatible. Nitinol may be used if the stent may be bent out of shape during insertion. A rigid outer shell in certain embodiments may be made of titanium or a hard biocompatible plastic like that of the casing of current artificial hearts such as The AbioCor Total Artificial Heart.

Additionally in selected embodiments with socks, the elastomeric fibers in the socks may be elastomeric polyurethane. Membranes may be made of elastomeric polyurethane. Such membranes are durable, biocompatible, and are capable of high strain and are used in current DeCDs and aortic balloons.

A patient with a heart that is growing aberrantly is in need of intervention to prevent progression to end-stage heart failure. If pharmacotherapy is ineffective, then cardiac assistance with a DeCD of the present invention may reverse the aberrant growth by inducing a beneficial type of deformation to the heart during systole. In some patients ventricular recovery (re-growth of a healthy heart) is even possible.

The present invention thus includes implanting DCCDs of the present invention in a patient in order to promote beneficial cardiac remodeling and growth or prevent myocyte apoptosis, or for other reasons beneficial to the patient. This implantation may be accompanied by other treatments, such as pharmacotherapy, pacing, electrical resynchronization, surgical reconstruction, stem cell therapy, gene therapy, and/or other therapies.

Methods of the present invention may also include using a DCCD of the present invention for systolic compression near the beginning of systolic ejection when the heart is full and its thickness-to-radius ratio is lowest. The length of systolic compression may be varied with the device used and the needs of the patient. In an exemplary embodiment, compression lasts between 55-60% of systolic duration. Similarly, the amount of pressure applied during compression may be varied depending upon the patient's needs.

The following examples are provided to further explain specific examples of the invention. They are not intended to represent all aspect of the invention in its entirety. Variations will be apparent to one skilled in the art.

EXAMPLES

Example 1

Formation of a Prototype DCCD A prototype of one embodiment of the present invention was built to fit a 110 kg bovine into which the device was implanted for an acute period (2 hours) to test the valve plane attachment and the preservation of cardiac curvature during assist with varying degrees of heart failure which was induced pharmacologically with high doses of a beta-blocker. Because the period of implantation was brief, biocompatible materials were not utilized; rather inexpensive and readily available materials were used. The methods of construction and sizing are directly applicable to devices for use in humans or other animals.

Figure 2A:
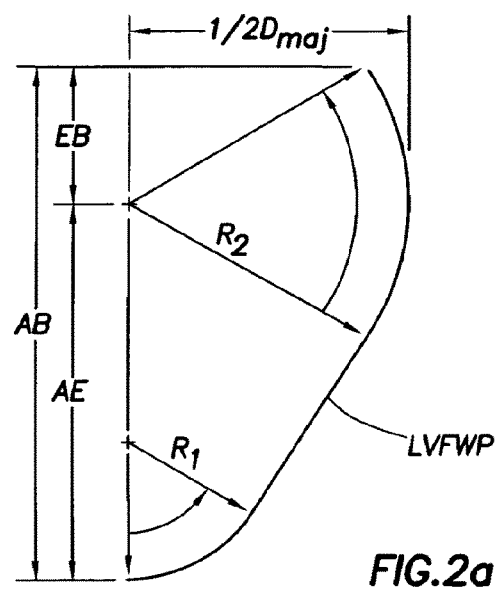
FIG. 2a represents 5 measurements of the bovine heart made by cardiac ultrasound and the Left Ventricle Free Wall Profile (LVFWP).

The size of this device was determined by 5 cardiac measurements—all of which can be made via a cardiac ultrasound. The major diameter ($D_{maj}$) and minor diameter ($D_{min}$) were obtained from a short axis view in the equatorial region. From a long axis view one can obtain: AB—distance from apex to base; EB—distance from equator (fattest part) to base; and $R_1$—radius of curvature of the apex. As diagrammed in FIG. 2a, these measurements were used to determine the LV Free Wall Profile (LVFWP) which consists of two circular arcs and a tangent to the arcs. $R_2=D_{maj}/2$ and AE=AB−EB. Thus, LVFWP depends solely on cardiac measurements.

Figure 2B:
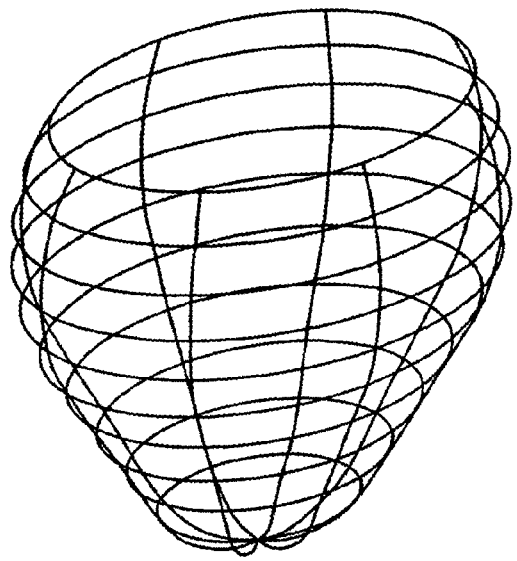
FIG. 2b represents a 3D shell generated by sweeping the LVFWP about an axis in a non-axis-symmetric manner.

To generate the 3-D shell in FIG. 2b, the LVFWP was swept about the axis in a non-axis-symmetric way. Let the LVFWP be the curve given by $R_p(Z)$ where $R_p$ is the distance from the axis and Z is the height along the axis (with z=0 at the apex). The shell surface is given by $$R(\theta, Z) = \left(\cos\theta + \frac{D_{min}}{D_{maj}}\sin\theta\right)R_p(Z)$$

Note that LVFWP is the trajectory with θ=0. This is consistent with cardiac coordinates (as detailed in Streeter, 1979) wherein θ=0 is taken as the central longitude of the LV free wall. Cross-sections of the shell were elliptical with their ellipticity being similar to that of the epicardial boundary in the equatorial region.

Figure 2C:
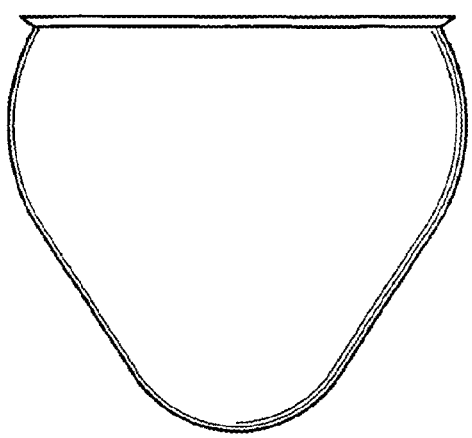
FIG. 2c depicts an outer shell of the prototype formed using matching molds with epoxy reinforced with fiberglass.

Rigid foam sheets were cut according to digitally rendered cross-sections and fixed together to form a plug mold. A lay-up of epoxy reinforced with fiberglass was applied to the plug mold and sawed in half (lengthwise) after curing. Each half was fixed to a separable right butt joint and multiple coats of hard wax were applied. Upon laying-up with fiberglass and a plywood cutout, the matching molds were formed. From these matching molds, the outer shell of the device (FIG. 2c) was made from epoxy reinforced with fiberglass (using a vacuum bag method to remove excess resin and to increase the fiber/matrix ratio).

Figure 2D:
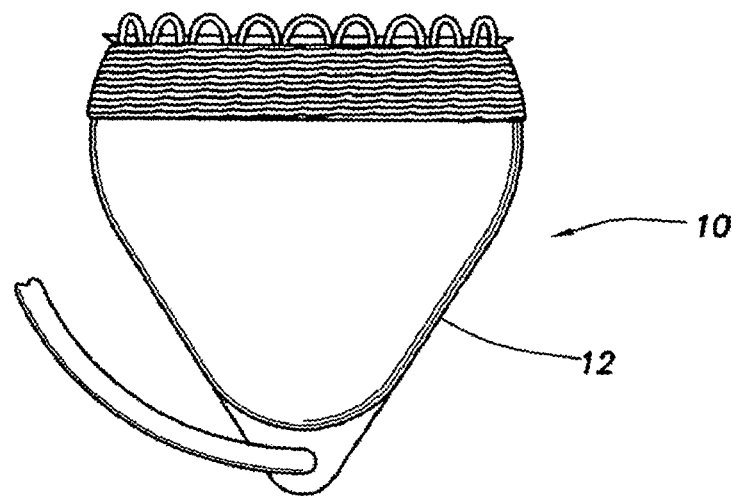
FIG. 2d depicts a side view of the completed prototype.
Figure 2E:
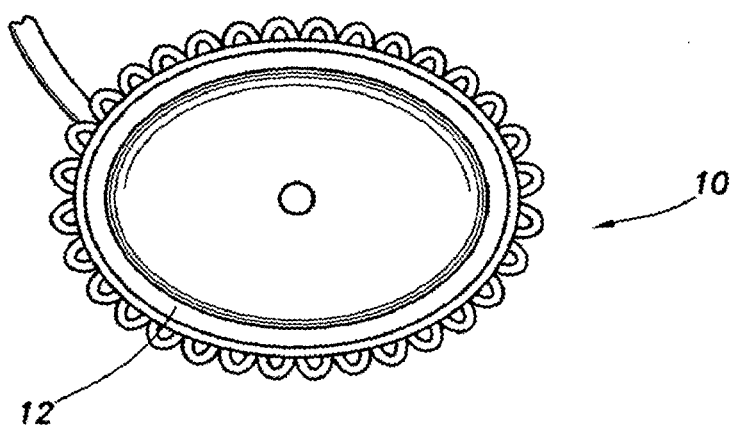
FIG. 2e depicts a top view of the completed prototype.

A brass, right-angle, hose barb was attached to the apex after making a hole in the shell. It was sealed and fixed in place via an epoxy/alumina composite. A cigar-shaped latex membrane was draped over the edges and held in place with a circumferential suture and cyanoacrylate glue. Suture loops were fastened out of nylon cord and affixed to the device with epoxy. Two profiles of the complete device are shown in FIGS. 2d & 2e.

Example 2

Attachment of a DCCD to the Heart

Figure 3:
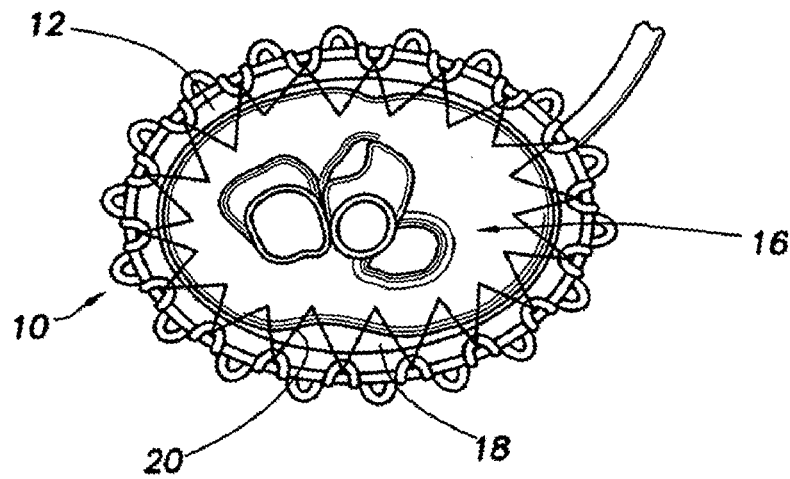
FIG. 3 illustrates a prototype embodiment of the DCCD of the present invention in which a bovine heart is attached. Running sutures form a complete ring of attachment. Half of the suture attachment loops are not used. The run patterns is: two forward loops while going through the tissue then back one loop before doing another forward bite.

Various methods of attaching the device to the heart have been tested using the fixed heart that was measured in order to determine the size of the device. As shown in FIG. 3, the heart was sewn to the device with running sutures that go completely around the heart. Although this is more laborious than a vacuum attachment method, other DCCDs require the device boundaries to be sutured to the heart and so a similar approach was tried here.

For animal models of CHF, the attachment in FIG. 3 is likely to be acceptable. Yet in CHF patients, such a method of attachment would be prone to surgical complications because there is too much pericardial fat and because of the need to sew near important vascular structures (e.g. left and right coronary arteries, great cardiac vein and coronary sinus). Moreover, the coronary sinus and right coronary arteries are on the posterior side of the heart, an area with limited exposure in-vivo.

Figure 4:
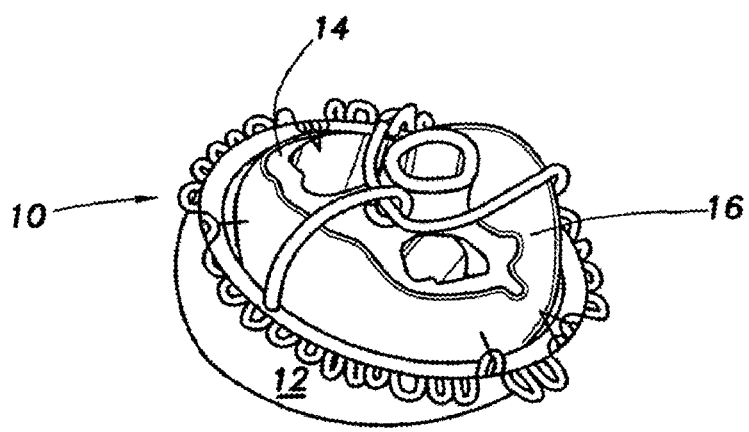
FIG. 4 illustrates a prototype embodiment of the DCCD of the present invention in which a bovine heart is attached. The method of attachment shown avoids sutures near the anterior and posterior interventricular sulci. The posterior stent would lie oblique to the pericardial sinus and go through the pericardial reflections to connect with an anterior stent that lies in the oblique pericardial sinus.

To reduce the chances of surgical complications and to increase the speed and ease of implantation, a second method of attachment was developed (see FIG. 4) using brief suture runs on the LV and RV free walls, which are areas with good exposure, fewer primary vessels, and less pericardial fat. A posterior stent begins in the oblique pericardial sinus and goes through pericardial reflections to connect with an anterior stent that lies in the transverse pericardial sinus. These stents keep the heart in the device via compression on the center of the valve plane which includes the commissure of aortic, mitral, and tricuspid valves.

In order to make the implantation easier and eliminate the need to access the posterior side of the heart, an alternative stenting method may be used with just an anterior stent that pushes on the center of the valve plane.

Example 3

Use of a DCCD

Experiments were performed using a device with an outer shell similar to that of the Hewson patent containing a plexiglass window in the outer shell to allow observation of the cardiac curvatures with a CCD camera while the device was in operation. The Hewson device was designed to be held in place by contact forces between the rim and the heart, but even active hearts are soft tissues that can undergo high shear and squeeze out of the device. Specifically, the myocardium of hearts are organized into sheets that allow contracting myocytes to rearrange and shear to attain high radial motions.

Thus when the DCCD similar to the Hewson device was implanted in a young bovine, even with a normal contractility, the heart readily escaped the device. Accordingly, the Hewson device, as described in the Herson patent, appears to be inoperable and required serious modification of the device and/or its means of attachment in order to develop an operable device.

Specifically, these experiments showed that the valve plane of the heart must be sewn to a Hewson type DCCD and then held in place with a stent that reaches from the device through the transverse pericardial sinus and pushes down on the commisure of the aortic and bicuspid valves. Attachment was as described above in Example 2 with the second option wherein the device was attached through partial suture to only the forward portion of the valve plane and not to the posterior as well because of difficulties in accessing the posterior of the heart.

Attempts using the stent alone without attachment to the valve plane were not successful and caused mitral regurgitation and allowed much of the heart to escape the device. Even with attachment to the valve plane and use of a stent, tricuspid regurgitation occurred, but the heart remained within the device. Tricuspid regurgitation may be prevented through a variety of modifications, including the implantation of a valve support that attaches to the device through a more uniform attachment such as tenting and suturing to the atrial appendages. Use of a fill suture to attach the device to the valve plane around the entire heart, rather than merely a partial suture as used in this experiment, may also prove beneficial.

More significantly, the DCCD, once able to retain the heart within itself during contraction, was observed to preserve natural cardiac curvatures.

Although the present invention and its advantages have been described in detail, it should be understood that various changes, substitutions and alterations can be made herein without departing from the spirit and scope of the invention as defined by the following claims.

What is claimed is:

1. A direct cardiac compression device adapted to surround the heart comprising:
    an outer shell comprising a basal annulus opposite an apical annulus and a series of rods that span between the basal annulus and the apical annulus to form a vase-shaped outer shell;
    an inner membrane in contact with the outer shell having a contour profile from a basal end to an apical end to surround the heart; and
    one or more contoured chambers formed between the outer shell and the inner membrane to selectively compress the heart to actively promote a contraction strain pattern characterized by non-inversion or lack of gross perturbation of the curvature on a diseased or damaged myocardium that promotes beneficial growth and remodeling of the myocardium.

2. The device of claim 1, wherein the outer shell, the inner membrane, or both are made of or more membranes.

3. The device of claim 1, wherein the series of rods comprises a series of adjustable rods to form an adjustable shell around the heart.

4. The device of claim 1, wherein the inner membrane comprises one or more metal stents.

5. The device of claim 1, wherein the outer shell comprises a rigid outer shell structure.

6. The device of claim 1, wherein the outer shell comprises an outer shell membrane, or mesh.

7. The device of claim 1, wherein the contour profile has a larger basal end contoured to a smaller apical end to surround the heart.

8. The device of claim 1, further comprising a connector adapted to secure the ventricular portion of the heart.

9. The device of claim 1, further comprising a device anchor adapted to secure the device about the valve plane of the heart.

10. The device of claim 1, further comprising a pneumatic drive operable to pressurize the inner membrane.

11. The device of claim 1, wherein the inner membrane comprises an elastomeric biocompatible material.

12. A method of assisting a diseased or damaged heart comprising the steps of:
    positioning a direct cardiac compression device around the heart, wherein the direct cardiac compression device comprises:
    an outer shell in contact with an inner membrane, wherein the outer shell comprises a basal annulus opposite an apical annulus and a series of rods that span between the basal annulus and the apical annulus to form a vase-shaped outer shell, and
    one or more contoured chambers formed between the outer shell and the inner membrane having a contour profile from a basal end to a apical end to surround the heart to selectively compress the heart to actively promote a contraction strain pattern characterized by non-inversion or lack of gross perturbation of the curvature on a diseased or damaged myocardium that promotes beneficial growth and remodeling of the myocardium;
    pressurizing selectively the direct cardiac compression device to compress the heart 1 during contraction without inverting or significantly perturbing the curvatures of the heart; and
    depressurizing selectively the direct cardiac compression device.

13. The method of claim 12, further comprising opening the chest cavity of a patient to provide access to the heart; and attaching the device of to the valve plane of the heart.

14. The method of claim 12, further comprising the step of further pressurizing selectively and depressurizing selectively the direct cardiac compression device to induce ventricular recovery in the heart.

15. The method of claim 12, further comprising the step of further pressurizing selectively and depressurizing selectively the direct cardiac compression device to prevent apoptosis of myocytes in the myocardium.

16. The method of claim 12, further comprising the step of further pressurizing selectively and depressurizing selectively the direct cardiac compression device to preserve the myocardium in a borderzone of a myocardial infarct.

17. A method of promoting growth and remodeling of the myocardium comprising the steps of:
    positioning a direct cardiac compression device around the heart, wherein the direct cardiac compression device comprises:
    an outer shell comprising a basal annulus opposite an apical annulus and a series of rods that span between the basal annulus and the apical annulus to form a vase-shaped outer shell, and
    an inner membrane in contact with the outer shell having a basal end contoured to a apical end to surround the heart, one or more contoured chambers formed between the outer shell and the inner membrane to selectively compress the heart to actively promote a contraction strain pattern characterized by non-inversion or lack of gross perturbation of the curvature on a diseased or damaged myocardium that promotes beneficial growth and remodeling of the myocardium;
    pressurizing selectively the direct cardiac compression device to compress the heart 1 during contraction without inverting or significantly perturbing the curvatures of the heart; and
    depressurizing selectively the direct cardiac compression device.

* * * * *